(12) United States Patent
Coates et al.

(10) Patent No.: US 7,875,734 B2
(45) Date of Patent: Jan. 25, 2011

(54) LOW PRESSURE CARBONYLATION OF HETEROCYCLES

(75) Inventors: Geoffrey W. Coates, Lansing, NY (US); John W. Kramer, Mt. Pleasant, MI (US); Joseph A. R. Schmidt, Sylvania, OH (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 12/486,158

(22) Filed: Jun. 17, 2009

(65) Prior Publication Data

US 2009/0287000 A1 Nov. 19, 2009

Related U.S. Application Data

(62) Division of application No. 11/705,528, filed on Feb. 13, 2007, now Pat. No. 7,569,709.

(60) Provisional application No. 60/780,884, filed on Mar. 10, 2006.

(51) Int. Cl.
*C07D 305/00* (2006.01)
(52) U.S. Cl. ...................................... 549/328
(58) Field of Classification Search ................... 549/328
See application file for complete search history.

(56) References Cited

U.S. PATENT DOCUMENTS

| | | | |
|---|---|---|---|
| 4,816,477 A | 3/1989 | Girotra et al. | |
| 6,133,402 A | 10/2000 | Coates et al. | |
| 6,852,865 B2 | 2/2005 | Coates et al. | |
| 7,304,172 B2 | 12/2007 | Coates et al. | |
| 7,569,709 B2 | 8/2009 | Coates et al. | |
| 2003/0162961 A1 | 8/2003 | Coates et al. | |
| 2006/0089252 A1 | 4/2006 | Coates et al. | |
| 2007/0213524 A1 | 9/2007 | Coates et al. | |
| 2007/0255039 A1 | 11/2007 | Coates et al. | |
| 2008/0108499 A1 | 5/2008 | Coates et al. | |

FOREIGN PATENT DOCUMENTS

| | | |
|---|---|---|
| DE | 1214211 | 4/1966 |
| JP | 10251190 | 9/1998 |
| JP | 10251241 | 9/1998 |
| JP | 2006284938 | 10/2006 |
| WO | WO 00/43000 | 7/2000 |
| WO | WO 2005/051944 | 6/2005 |
| WO | WO 2005/068420 | 7/2005 |

OTHER PUBLICATIONS

Knunyants et al, Fluorine-containing beta-lactone.II. Beta-trifluoromethyl-beta-methyl-beta-propiolactone, Izrestiya Akademii Nauk SSSR, Seriya Khimicheskaya, 1961, 808-10, abstract page.*
Schmidt et al , Chromium(III) Octaethylporphyrinato Tetracarbonylcobaltate: a highly active selective , and versatile catalyst for expoxide carbonylation, Journal of American Chemical Society, 2005, 127(32), p. 11426-11435.*
Kramer, et al., "Practical β-Lactone Synthesis: Epoxide Carbonylation at 1 atm," *Org. Lett.* 2006, 8(17), 3709-3712.
Getzler et al., "Catalytic Carbonylation of β-Lactones to Succinic Anhydrides," J. Am. Chem. Soc. 2004, 126, 6842-6843.
Nelson, et al., "Divergent reaction pathways in amine additions to β-lactone electrophiles. An application to β-peptide synthesis," Tetrahedron 58, 2002, 7081-7091.
Tsuda, et al., cis,cis- and trans,trans-1-Methyl-4-hydroxy-3,5-bis(äthoxycarbonylmethyl)piperidin, Chem Pharm Bull 1959, 2, 199.
Angelis, et al., "Inversion of Configuration of (S)-β-Hydroxy-y-butyrolactone with Total Retention of the Enantiomeric Purity", Eur. J. Org. Chem. 1999, 2705-2707.
Nelson, et al., "Catalytic Asymmetric Acyl Halide-Aldehyde Cyclocondensations. A Strategy for Enantioselective Catalyzed Cross Aldol Reactions", J. Am. Chem. Soc. 1999, 121, 9742.
Nelson, et al., "A de Novo Enantioselective total Synthesis of (-)-Laulimalide", J. Am. Chem. Soc., 2002, 124, 13654-13655.
Zhu, et al., Cinchona Alkaloid-Lewis Acid Catalyst Systems for Enantioselective Ketene-Aldehyde Cycloadditions, J. Am. Chem. Soc., 2004, 126, 5352-5353.
Dingwall, et al., "Free Radical Catalysed Additions to the Double Bond of Diketene: A Synthesis of Novel oxetan-2-ones", J. Chem. Soc. Perkin Trans. I, 1986, 2081-2090.
Tennyson, et al., "Use of In Situ Generated Ketene in the Wynberg β-Lactone Synthesis: New Transformations of the Dichlorinated β-Lactone Products", J. Org. Chem., 2000, 65, 7248-7252.

(Continued)

*Primary Examiner*—Taylor Victor Oh
(74) *Attorney, Agent, or Firm*—Brenda Herschbach Jarrell; Charles E. Lyon; Danielle M. Nihan

(57) ABSTRACT

Heterocycles, e.g., epoxides, are carbonylated at low pressure with high percentage conversion to cyclic, ring expanded products using the catalyst

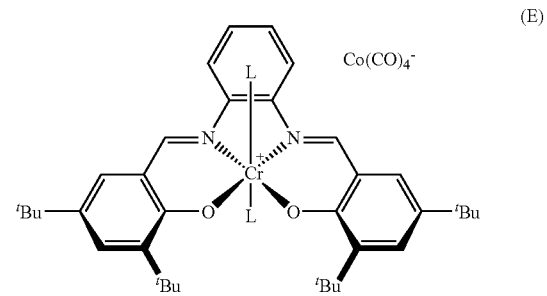

where L is tetrahydrofuran (THF).

8 Claims, No Drawings

OTHER PUBLICATIONS

Lee, et al., "Synthesis of β-Lactones by the Regioselective, Cobalt and Lewis Acid Catalyzed Carbonylation of Simple and Functionalized Epoxides", J. Org. Chem., 2001, 66, 5424-5426.

Bizzarri, et al., "Influence of Structural Parameters on the Ring-Opening Polymerization of New Alkyl Malolactonate Monomers and on the Biocompatibility of Polymers Therefrom", Macromol. Chem. Phys., 2002, 203, (10-11) 1684-1693.

Bizzarri, et al., "Synthesis and Characterization of New Malolactonate Polymers and Copolymers for Biomedical Applications", Macromolecules, 2002, 35, 1215-1223.

Nelson, et al., "Catalytic Asymmetric Acyl Halide Aldehyde Cyclocondensation Reaction", Organic Synthesis, vol. 82, p. 170-178, 2005; Coll. vol. 11, p. 506-513, 2009.

Schmidt, et al., "A Readily Synthesized and Highly Active Epoxide Carbonylation Catalyst Based on a Chromium Porphyrin Framework: Expanding the Range of Available β-Lactones", Organic Letters, 2004, vol. 6, No. 3, 373-376.

Leboucher-Durand, et al., "4-Carboxy-2-oxetanone as a new chiral precursor in the preparation of functionalized racemic or optically active poly(malic acid) derivatives", Polymer Bulletin 36, 35-41, 1996.

Barbaud, et al., "Poly(β-malic acid) derivatives with non-charged hydrophilic lateral groups: synthesis and characterization", Polymer Bulletin 43, 297-304, 1999.

Moine, et al., "Polymers of malic acid conjugated with the 1-adamantyl moiety as lipophilic pendant group", Polymer, vol. 38, No. 12, pp. 3121-3127, 1997.

White, et al., "Addressing the Competition Between Intramolecular Acyl and Beta Ring Cleavage in β-Lactones", Tetrahedron Letters, vol. 38, No. 13, pp. 2223-2226, 1997.

Reid, et al., "A stannous chloride-induced deacetalisation-cyclisation process to prepare the ABC ring system of 'upenamide", Tetrahedron Letters, 45, 2004, 4181-4183.

Lin, et al., "Predicting the RIS absolute configuration in asymmetric bifunctional catalysis (ABC)" Tetrahedron Letters, 48, 2007, 5275-5278.

Ito, et al., "Preparation and Use of Novel (S)-β-propiolactone as a Chiral Fluorinated Building Block", Tetrahedron, 54, 1998, 5523-5530.

Tidwell, T. T. Science of Synthesis, 2006, 23, 15-51.

Ito, T., "Application of Optically Active β-Trihalomethyl-β-Propiolactones toward Biologically Active Compounds by their Development of Novel Carbon-Carbon Bond Formation", Research Reports of the Faculty of Engineering, Mie University, 1999, 24, 113-114.

Cammas-Marion, S. et al.,"Poly(β-malic acid) homo- and copolymers synthesis and their use for the preparation of nanoparticles." Proceedings of the International Symposium on Controlled Release of Bioactive Materials, 2000, 27, 650-651.

Leboucher-Durand, M. et al., "Poly(β-malic acid) derivatives with unsaturated lateral groups: epoxidation as model reaction of the double bonds reactivity." Reactive & Functional Polymers, 1996, 31(1), 57-65.

Fujishiro, K. et al., "Liquid-crystalline properties of chiral malolactinate monomers and their comb-shaped polymers." Liquid Crystals, 1992, 12(4), 561-73.

Arnold, S.C., et al., "Synthesis of stereoregular poly(alkyl malolactonates)." Makromolekulare Chemie, Macromolecular Symposia, 1986, 6, 285-303.

Araki, T., et al., "isomerization ploymerization of βpropiolactones carrying side-chain ester groups." Journal of Polymer Science, Polymer Chemistry Edition, 1983, 21(6), 1671-9.

Araki, T. et al., "Selective synthesis of structurally isomeric poly-β-ester and poly-σ-ester from β-(2-acetoxyethyl)-β-propiolactone with aluminum and zinc catalysts." Journal of Polymer Science, Polymer Chemistry Edition 1982, 20(12), 3337-50.

Araki, T. et al., "Selective synthesis of structurally isomeric poly(β-ester) and poly(σ-ester) from β(2-acetoxyethyl)-βpropiolactone. A new difference between (etAIO)$_n$ and Et(ZnO)$_2$ZnEt catalyses." journal of Polymer Science, Polymer Letters Edition, 1978, 16(10), 519-23.

Vulfson, N.S., et al., "β-Lactones and β-lactonoacids. III. Condensation of citral with malonic acid." Zhurnal Obshchei Khimii, 1943, 13, 436-47.

Suzuki M., "Analytical aspects of endogenous sugar-derived compunds: special emphasis on inductive agents to hunger or satiety." GC-MS News, 1985, 13(2), 41-4.

Hyatt, et al., "Organic Reactions", 1994, 45, Chapter 2.

\* cited by examiner

LOW PRESSURE CARBONYLATION OF HETEROCYCLES

CROSS-REFERENCES TO RELATED APPLICATIONS

This application is a divisional of U.S. Ser. No. 11/705,528, filed Feb. 13, 2007, which claims benefit of U.S. Ser. No. 60/780,884, filed Mar. 10, 2006. The entire contents of each of these priority applications are hereby incorporated by reference.

This invention was made at least in part with U.S. Government support under National Science Foundation Grant No. CHE-0243605 and Department of Energy Grant No. DE-FG02-05ER15687 and the National Institutes of Health Chemical Biology Interface (CBI) Training Grant. The U.S. Government has certain rights in the invention.

FIELD OF THE INVENTION

The invention is directed to catalytic carbonylation of epoxides, aziridines, thiiranes, oxetanes, lactones, lactams and analogous compounds.

BACKGROUND OF THE INVENTION

U.S. Pat. No. 6,852,865 is directed to carbonylation of epoxides, aziridines, thiiranes, oxetanes, lactones, lactams and analogous compounds in the presence of a catalytically effective amount of catalyst having the general formula $[\text{Lewis acid}]^{z+}\{[QM(CO)_x]^{w-}\}_y$, where Q is any ligand and need not be present, M is a transition metal selected from the group consisting of Groups 4, 5, 6, 7, 8, 9 and 10 of the periodic table of elements, z is the valence of the Lewis acid and ranges from 1 to 6, w is the charge of the metal carbonyl and ranges from 1 to 4 and y is a number such that w times y equals z, and x is a number such as to provide a stable anionic metal carbonyl for $\{[QM(CO)_x]^{w-}\}_y$, and ranges from 1 to 9 and typically from 1 to 4. CO pressures ranging from 100 to 1000 psig are disclosed. High percentage conversions were obtained at CO pressures of 800 psig and 900 psig; these pressures require the use of a high pressure reactor.

SUMMARY OF THE INVENTION

It has been found herein that high percentage conversions can be obtained with low CO pressures when a particular catalyst (A) as described below is utilized.

The invention herein is directed to carbonylation of a compound having the formula:

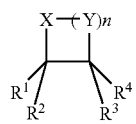

(I)

where $R^1$, $R^2$, $R^3$ and $R^4$ are the same or different and are each selected from the group consisting of a hydrogen atom, a halogen atom, a carbon-containing group, a fluorine containing group, a heterocyclic compound residue, an oxygen-containing group, a nitrogen-containing group, a boron-containing group, a sulfur-containing group, a phosphorus-containing group, a silicon-containing group, and two or more of these can be bonded to each other to form a ring or rings, and X is selected from the group consisting of O, S and $NR^5$, where $R^5$ is selected from the group consisting of a hydrogen atom, a halogen atom, a carbon-containing group, a fluorine-containing group, a heterocyclic compound residue, an oxygen-containing group, a nitrogen-containing group, a boron-containing group, a sulfur-containing group, a phosphorus-containing group, and a silicon-containing group, and where n is 0 or 1, and Y is C=O or $CH_2$, said process comprising the step of reacting compound (I) with carbon monoxide under a pressure enabling reaction in glassware, e.g., a pressure ranging from ambient pressure (e.g., 1 atmosphere) to 125 psig, in the presence of a catalytically effective amount of a catalyst (A), described below, to form a product having the structural formula:

(II)

where $R^1$, $R^2$, $R^3$ and $R^4$ and X correspond to $R^1$, $R^2$, $R^3$ and $R^4$ and X in (I) including two or more of $R^1$, $R^2$, $R^3$ and $R^4$ forming a ring if that is the case for (I); and in the case where n for (I) is 0, n for (II) is 0, 1 or 2, and in the case where n for (I) is 1, n for (II) is 1 or 2.

$R^1$, $R^2$, $R^3$, $R^4$ and $R^5$ can also be any other functionality that the catalyst referred to below is tolerant of. The term "any other functionality that the catalyst referred to below is tolerant of" is used herein to mean that the functionality can be present without causing the catalyst to be inactive.

The catalyst (A) has the formula:

(A)

$k[QM'(CO)_y]^{z-}[M(JR_q)_m]^{p+}$ where k is an integer ranging from 1 to 6, Q can be present or absent and is any ligand bound to M' and if present, is selected from the group consisting of a phosphine group, phosphite, group comprising pyridine moiety, $C_1$-$C_{30}$ alkyl, $C_6$-$C_{30}$ aryl, $C_1$-$C_{30}$ acyl, and carbene, such that a stable metal complex is formed, M' is a metal from groups 4-10 of the periodic table, y is an integer ranging from 0 to 6, z is the charge on the anionic portion and ranges from 1 to 4, M is selected from the group consisting of a metal atom from groups 2-15 of the periodic table, lanthanides and actinides, J is selected from the group consisting of a hydrogen atom, a halogen atom, a carbon atom, a nitrogen atom, a sulfur atom, a phosphorus atom, and an oxygen atom, R is optionally present and, if present, is a hydrogen atom or a carbon-containing group containing 1 to 30 carbon atoms, q is an integer ranging from 0 to 3, m is an integer ranging from 0 to 6 and p is the charge on the cationic portion and is equal to the product of k and z.

The catalyst of these denoted (E), found to be best, has the structural formula.

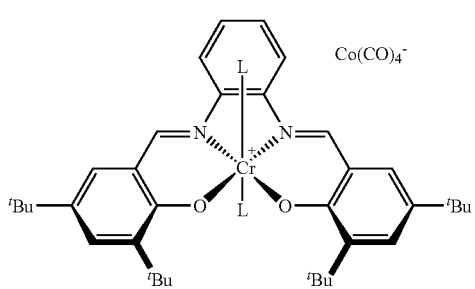

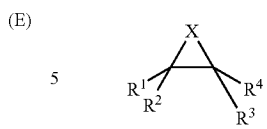

where L is tetrahydrofuran (THF).

The reaction is preferably carried out in glassware. As used herein "glassware" means, for example, a glass reactor, for example, a Fisher Porter bottle, at 100 psig, or a round bottom glass flask, a glass vial or other glass vessel that can hold 1 atmosphere of CO.

As used herein the term "halogen atom" includes, for example, a chlorine atom, a fluorine atom, an iodine atom, or a bromine atom.

As used herein the term "high percentage conversion" means at least 40% conversion. The percent conversion to (II) is preferably 90% or more, very preferably 95% or more.

A second embodiment herein is directed to carbonylation of a compound having the structure (I) as defined for the first embodiment, comprising reacting Compound (I) with carbon monoxide in a reactor that does not comprise stainless steel. The advantage of this is that nickel and iron are present in stainless steel and nickel and iron carbonyls formed during carbonylation inside a reactor are highly toxic.

DETAILED DESCRIPTION

We turn now to further description of $R^1$, $R^2$, $R^3$, $R^4$ and $R^5$ for (I) and (II). The carbon containing group can be, for example, $C_1$-$C_{100,000}$ alkyl, $C_2$-$C_{100,000}$ alkenyl and $C_6$-$C_{100,000}$-aryl, or alkaryl containing from 1 to 20 carbon atoms; these are optionally substituted, for example, with halogen (including, for example, substitution of fluorine atom on one or more carbons and/or substitution of one or more trifluorocarbon groups) or with benzyl ether. The oxygen-containing group can be, for example, ester-containing moiety containing from 1 to 20 carbon atoms, ketone containing moiety containing from 1 to 20 carbon atoms, alcohol containing moiety containing from 1 to 20 carbon atoms, an acid containing moiety containing 1 to 20 carbon atoms, or an aldehyde containing moiety containing 1 to 20 carbon atoms and can be an ether containing moiety where the ether group contains from 1 to 20 carbon atoms and can be oxygen-containing (in addition to the ether oxygen) or can be a benzyl ether or can be a glycidyl ester where the ester group can be $C_1$-$C_{20}$ alkyl, $C_2$-$C_{20}$ alkenyl, $C_6$-$C_{20}$ aryl or $C_6$-$C_{20}$ arylalkyl. The nitrogen-containing group, can contain, for example, from 1 to 20 carbon atoms and contain an amide moiety. The sulfur-containing group can contain, for example, 1 to 20 carbon atoms and can be or contain tosyl group or contain tosyl moiety or be or contain a sulfonate group. The silicon-containing group can be, for example, alkyl substituted silyl ether where the ether group is $C_1$-$C_6$ alkylene and alkyl substitution consists of one to three $C_1$-$C_6$ alkyl, substituted on silyl.

In one case, n for (I) is 0 so that the structural formula for (I) becomes:

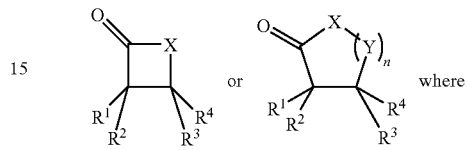

and the product has the structural formula:

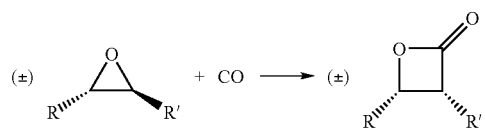

n is 1 and Y is C=O.

In a subset (a) of this case carried out at CO pressure of 100 psig (6.8 atm), the reaction equation is:

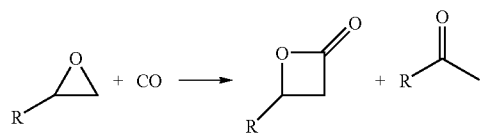

where R is the same as $R^3$ above and R' is the same as $R^1$ above.

In a subset (b) of this case carried out at CO pressure of 1 atmosphere (0 psig), the reaction equation is:

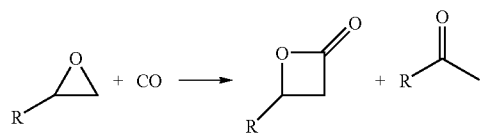

where R is the same as $R^3$ above.

The subset (a), that is the 100 psig CO pressure case, requires special glassware, e.g., a Fisher-Porter bottle, but gives essentially no side products The special glassware is much less expensive than the high pressure reactor used in examples in U.S. Pat. No. 6,852,865.

The subset (b), that is the 1 atm CO pressure case, can use a glass roundbottom flask or other glassware, for example, a glass vial or other glass vessel that can hold 1 atmosphere of CO, but results in some side products as indicated in Kramer, J. W., et al., Org. Lett. 8(17), 3709-3712 (Jul. 18, 2006), the whole of which is incorporated herein by reference.

We turn now to the catalysts.

A preferred catalyst (A) is catalyst (B) which has the structural formula:

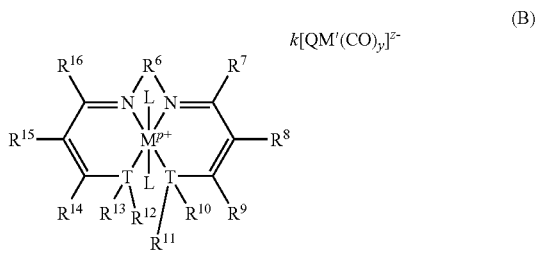

(B)

where M, p and $k[QM'(CO)_y]^{z-}$ are the same as for (A), each T can be the same or different and is selected from the group consisting of a sulfur atom, an oxygen atom, a nitrogen atom or a phosphorus atom; $R^{12}$, $R^{13}$, $R^{10}$ and $R^{11}$ are optional and are each selected form the group consisting of a hydrogen atom, a halogen atom, a carbon-containing group containing 1 to 30 carbon atoms, a heterocyclic compound residue, an oxygen-containing group, nitrogen-containing group, a boron-containing group, a sulfur-containing group, a phosphorus-containing group, a silicon-containing group, and two or more of them can be bonded to each other to form a ring or rings, and $R^{14}$, $R^{15}$, $R^{16}$, $R^6$, $R^7$, $R^8$ and $R^9$ are each a hydrogen atom, a carbon-containing group containing 1-30 carbon atoms, a heterocyclic compound residue, an oxygen-containing group, a nitrogen-containing group, a boron-containing group, a sulfur-containing group, a phosphorus-containing group, or a silicon-containing group, except that $R^6$ is not a hydrogen atom and two or more of them and $R^{10}$, $R^{11}$ and $R^{12}$ and $R^{13}$ can be bonded to each other to form a ring or rings; and L is a Lewis base, which can be absent, and if present, each L is the same or different and is selected from the group consisting of ethers (e.g., tetrahydrofuran), thioethers, esters, amines, pyridines, phosphines, phosphites, nitrites and carbenes.

A preferred catalyst (B) is catalyst (C), which has the structural formula:

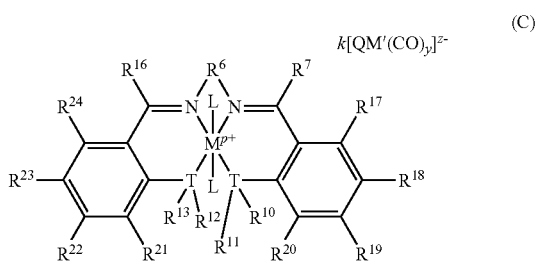

(C)

where M, T, p, $k[QM'(CO)_y]^{z-}$, $R^{12}$, $R^{13}$, $R^{10}$, $R^{11}$, $R^{16}$, $R^6$, $R^7$ and L are the same as for (B), and $R^{21}$, $R^{22}$, $R^{23}$, $R^{24}$, $R^{17}$, $R^{18}$, $R^{19}$ and $R^{20}$ are the same or different and are each selected from the group consisting of a hydrogen atom, a halogen atom, a carbon-containing group containing from 1 to 30 carbon atoms, a heterocyclic compound residue, an oxygen-containing group, a nitrogen-containing group, a boron-containing group, a sulfur-containing group, a phosphorus-containing group, a silicon-containing group, and two or more of them and $R^6$, $R^7$, $R^{10}$, $R^{11}$, $R^{12}$, $R^{13}$ and $R^{16}$ can be bonded to each other to form a ring or rings.

A preferred catalyst (C) is catalyst (D) which has the structural formula:

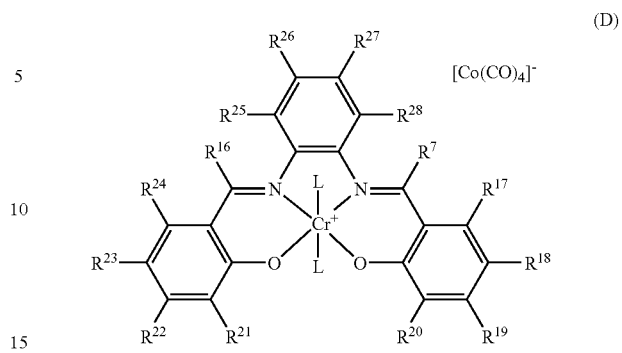

(D)

where $R^{16}$, $R^7$, $R^{21}$, $R^{22}$, $R^{23}$, $R^{24}$, $R^{17}$, $R^{18}$, $R^{19}$, $R^{20}$ and L are the same as for (C) and $R^{25}$, $R^{26}$, $R^{27}$ and $R^{28}$ are the same or different and are selected from the group consisting of a hydrogen atom, a halogen atom, a carbon-containing group containing 1 to 30 carbon atoms, a heterocyclic compound residue, an oxygen-containing group, a nitrogen-containing group, a boron-containing group, a sulfur-containing group, a phosphorus-containing group, a silicon-containing group, and two or more of them and $R^{16}$, $R^7$, $R^{21}$, $R^{22}$, $R^{23}$, $R^{24}$, $R^{17}$, $R^{18}$, $R^{19}$ and $R^{20}$ can be bonded to each other to form a ring or rings.

Catalyst G1 described in U.S. Pat. No. 6,852,865, that is $[Cp_2Ti(THF)_2][Co(CO)_4]$ where Cp means cyclopentadienyl has been found not to work at all for epoxide carbonylation carried out at CO pressures of 100 psig and below and is excepted from the catalysts herein.

The catalyst (A) herein can be made by reaction of $M(JR_q)$ X' where $M(JR_q)$ is defined as for catalyst (A) with $QM'(CO)_y$—Y' where $QM'(CO)_y$ is defined as for catalyst (A) and X' is any leaving group and Y' is a moiety that will form a salt with X'.

We turn now to the catalyst (E). It is readily made as described in Supporting Information for Kramer, J. W., et al., Org. Lett. 8(17), 3709-3712 (Jul. 18, 2006), the whole of which is incorporated herein by reference.

We turn now to the reaction conditions besides starting material, CO pressure and catalyst.

The mole ratio of component (I) charged to catalyst charged, can range, for example, from 1:1 to 10,000:1, for example, from 25:1 to 150:1. For subset (a), the mole ratio used in the examples was 100:1, for subset (b), the mole ratio used in the examples was 50:1.

Where the CO pressure is greater than 1 atm, e.g., when it is 100 psig, the pressure and the volume of the reactor define the amount of CO. Where the CO pressure is one atmosphere, the amount of CO is provided by the headspace in the reactor which is, for example, 200 to 1000 ml.

The solvent for the reaction used in experiments herein was dimethoxyethane (DME). Other useful solvents include diglyme, triglyme, tetrahydrofuran and toluene. The reaction may be carried out in any solvent in which the starting material and catalyst are at least partially soluble.

The reaction can be carried out at room temperature.

The time of reaction can range, for example, from 1 minute to 50 hours or even longer. The reactions of subset (a) obtained clean carbonylation to the corresponding beta-lactone within three hours. The reactions of subset (b) were carried out for 6 hours.

Elements of the invention and working examples are set forth in Kramer, J. W., Lobkovsky, E. B., and Coates, G. W., Org. Lett. 8(17), 3709-3712 (Jul. 18, 2006), the whole of which is incorporated herein by reference.

We turn now to the second embodiment herein.

It has been documented that stainless steel and CO produce $Fe(CO)_5$ and $Ni(CO)_4$ (See Shriver, D., et al., Inorganic Chemistry, W. Friedman and Co., 1990, page 508) which are both very toxic. Carbonylation reactions run in other types of reactors do not have this problem. These other reactors can comprise as material of construction, for example, glass, plastic, aluminum or brass. The glass reactors can be, for example, a Fisher Porter bottle, for reaction at 100 psi, or a round bottom glass flask or glass vial or other glass vessel that can hold 1 atm of CO for reactions at 1 atm.

The invention is illustrated in the following working examples.

Carbonylation Example I

Epoxide carbonylation was carried out with 100 psig CO using catalyst E, according to the process of subset (a) described above. As indicated above, the reaction equation for subset (a) is

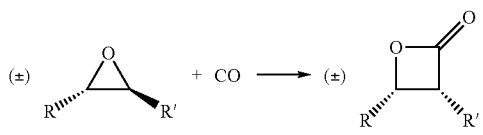

where R is the same as $R^3$ above and R' is the same as $R^1$ above. Conditions and results are set forth in Table 1 below.

TABLE 1

| Entry | R | R' | t[h] | Conv.[b] [%] |
|---|---|---|---|---|
| 1 | Me | H | 2 | 99 |
| 2 | Et | H | 1 | 99 |
| 3 | $(CH_2)_9CH_3$ | H | 2 | 99 |
| 4 | $(CH_2)_2CH=CH_2$ | H | 2 | 99 |
| 5 | $CH_2OCH_2CH=CH_2$ | H | 1 | 99 |
| 6 | $CH_2O^nBu$ | H | 1 | 99 (88)[c] |
| 7 | $CH_2OSiMe_2{}^tBu$ | H | 1 | 99 |
| 8 | $CH_2OC(O)CH_3$ | H | 2 | 99 |
| 9 | $CH_2OC(O)Ph$ | H | 3 | 99 |
| 10 | $CH_2Cl$ | H | 3 | 99 |
| 11[d] | Me | Me | 8 | 99[e] |

[a]All reactions were stirred in a Fisher-Porter bottle using 2 mmol epoxide in 2 mL DME and 1 mol % 1 at RT, unless noted otherwise
[b]Conversion determined by $^1H$ NMR spectroscopy (and confirmed by GC for entry 1); β-lactone was exclusive product.
[c]Isolated yield from one-gram scale reaction.
[d]2 mol % 1.
[e]Product was cis-3,4-dimethyl-2-propiolactone.

Carbonylation Example II

Epoxide carbonylation was carried out with 1 atmosphere CO, according to the process of subset (b) described above. As indicated above, the reaction equation for subset (b) is

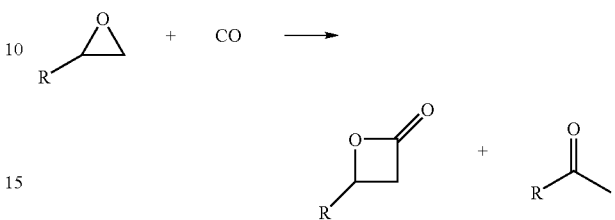

where R is the same as $R^3$ above.

Conditions and results are set forth in Table 2 below.

TABLE 2

| Entry | R | Conv.[b] [%] | β-Lactone: Ketone[b] |
|---|---|---|---|
| 1 | Me | 99 | 96:4 |
| 2 | Et | 99 | 97:3 |
| 3 | $(CH_2)_9CH_3$ | 99 | 99:1 |
| 4 | $(CH_2)_2CH=CH_2$ | 99 | 95:5 |
| 5 | $CH_2OCH_2CH=CH_2$ | 99 | 93:7 |
| 6 | $CH_2O^nBu$ | 99 | 89:11 |
| 7 | $CH_2OSiMe_2{}^tBu$ | 99 | 96:4 |
| 8 | $CH_2OC(O)CH_3$ | 99 | 95:5 |
| 9 | $CH_2OC(O)Ph$ | 89[c] | 95:5 |
| 10 | $CH_2Cl$ | 35[c] | 89:11 |

[a]Carbonylation reactions performed in a CO-filled, 500-mL round-bottom flask with 2 mmol epoxide, 2 mL DME, and 2 mol % 1 stirred at RT for six hours
[b]Conversion and product ratios determined by $^1H$ NMR spectroscopy
[c]Remainder was unreacted epoxide

Carbonylation Example III

Epoxide carbonylation was carried out using Catalyst E at 100 psi CO according to the procedure of Carbonylation Example I except using epoxide and reaction time and providing lactone product and yield percent as set forth in Table 3 below.

TABLE 3

| Entry | Epoxide | Time (h) | Yield (%) | Lactone |
|---|---|---|---|---|
| 12 |  | 2.5 | 99 |  |

TABLE 3-continued

| Entry | Epoxide | Time (h) | Yield (%) | Lactone |
|---|---|---|---|---|
| 13 | Ph-CH₂-O-CH₂CH₂-(epoxide) | 1.5 | 99 | Ph-CH₂-O-CH₂CH₂-(β-lactone) |
| 14 | Ph-CH₂-O-(CH₂)₄-(epoxide) | 20 | 99 | Ph-CH₂-O-(CH₂)₄-(β-lactone) |
| 15 | 4-MeO-C₆H₄-CH₂-(epoxide) | 1.5 | 99 | 4-MeO-C₆H₄-CH₂-(β-lactone) |
| 16 | furfuryl-O-CH₂-(epoxide) | 23 | 99 | furfuryl-O-CH₂-(β-lactone) |
| 17 | cyclooctene oxide | 24 | 20 | bicyclic β-lactone |
| 18 | methacryloyloxymethyl epoxide | 1 | 91 | methacryloyloxymethyl β-lactone |
| 19 | MsO-CH₂-(epoxide) | 6 | 37 | MsO-CH₂-(β-lactone) |
| 20 | 1,3-dioxolan-2-yl-(CH₂)ₙ-(epoxide) | 2.5 | 99 | 1,3-dioxolan-2-yl-(CH₂)ₙ-(β-lactone) |
| 21 | Me₂N-C(O)-(CH₂)ₙ-(epoxide) | 3 | 73 | Me₂N-C(O)-(CH₂)ₙ-(β-lactone) |
| 22 | iPr₂N-C(O)-(CH₂)ₙ-(epoxide) | 24 | 85 | iPr₂N-C(O)-(CH₂)ₙ-(β-lactone) |
| 23 | | 24 | 71 | |

Variations

The foregoing description of the invention has been presented describing certain operable and preferred embodiments. It is not intended that the invention should be so limited since variations and modifications thereof will be obvious to those skilled in the art, all of which are within the spirit and scope of the invention.

What is claimed is:

1. A compound of formula:

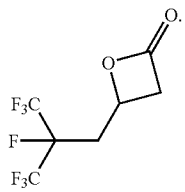

2. A compound of formula:

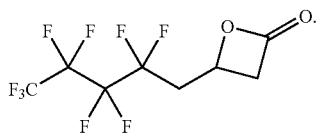

3. A compound of formula:

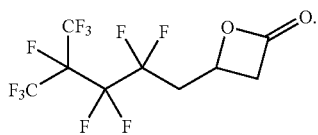

4. A compound of formula:

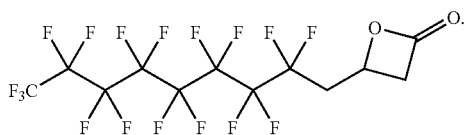

5. A compound of formula:

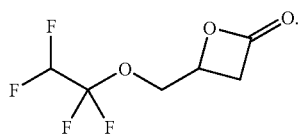

6. A compound of formula:

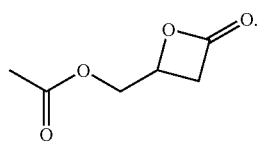

7. A compound of formula:

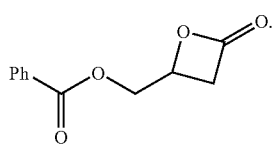

8. A compound of formula:

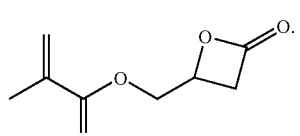

* * * * *